(12) United States Patent
Sakata (10) Patent No.: US 9,016,583 B2
(45) Date of Patent: Apr. 28, 2015

(54) CODE READING DEVICE AND DATA COLLECTION SYSTEM USING THE SAME

(75) Inventor: Tetsuya Sakata, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 887 days.

(21) Appl. No.: 12/525,234

(22) PCT Filed: Feb. 5, 2009

(86) PCT No.: PCT/JP2009/051979
§ 371 (c)(1),
(2), (4) Date: Jul. 30, 2009

(87) PCT Pub. No.: WO2009/099148
PCT Pub. Date: Aug. 13, 2009

(65) Prior Publication Data
US 2011/0204133 A1     Aug. 25, 2011

(30) Foreign Application Priority Data

Feb. 7, 2008    (JP) .................................. 2008-027358

(51) Int. Cl.
*G06K 7/10* (2006.01)
*A61B 5/145* (2006.01)
(Continued)

(52) U.S. Cl.
CPC ......... *A61B 5/14532* (2013.01); *G06F 19/3418* (2013.01); *G06Q 10/10* (2013.01); *G06Q 50/22* (2013.01); *G01N 33/48771* (2013.01); *A61B 2562/08* (2013.01); *A61B 2562/085* (2013.01)
USPC ................... 235/472.01; 235/462.01

(58) Field of Classification Search
CPC .......... G06K 7/10881; G06K 7/10851; G06K 17/0022
USPC ........................... 235/462.01, 472.01; 702/62
See application file for complete search history.

(56) References Cited

U.S. PATENT DOCUMENTS

| 5,371,687 A | 12/1994 | Holmes, II et al. |
| 5,507,288 A | 4/1996 | Bocker et al. |

(Continued)

FOREIGN PATENT DOCUMENTS

| CN | 1791897 A | 6/2006 |
| JP | 62-209684 | 9/1987 |

(Continued)

OTHER PUBLICATIONS

Extended European Search Report issued in corresponding European Patent Application No. 09708580.7 dated May 23, 2012.

(Continued)

*Primary Examiner* — Rafferty Kelly
(74) *Attorney, Agent, or Firm* — Morgan, Lewis & Bockius LLP (57) ABSTRACT

The present invention provides a code reading device capable of associating various kinds of information with obtained data with ease simply by connecting the code reading device to a data holding device. A code reading device (1) includes a code reader (15) for reading code information, a memory (31), and a data processing control portion (32). The data processing control portion (32) stores code information read by the code reader in a code information storage area (311) of the memory (31), reads data from a data holding device when the data holding device is connected to the code reading device and stores the data in a data storage area (312) of the memory (31), and sends to a personal computer the data in the data storage area (312) in a state of being associated with the code information in the code information storage area (311) when the personal computer is connected to the code reading device.

19 Claims, 8 Drawing Sheets

(51) Int. Cl.
*G06F 19/00* (2011.01)
*G06Q 10/10* (2012.01)
*G06Q 50/22* (2012.01)
*G01N 33/487* (2006.01)

(56) References Cited

U.S. PATENT DOCUMENTS

| | | | |
|---|---|---|---|
| 6,217,744 | B1 | 4/2001 | Crosby |
| 7,545,272 | B2 * | 6/2009 | Goodnow et al. .......... 340/572.1 |
| 2002/0060247 | A1 * | 5/2002 | Krishnaswamy et al. ................. 235/472.01 |
| 2004/0087894 | A1 | 5/2004 | Flaherty |
| 2006/0129356 | A1 | 6/2006 | Nakamoto et al. |
| 2007/0142822 | A1 | 6/2007 | Remde |
| 2007/0231846 | A1 * | 10/2007 | Cosentino et al. .............. 435/14 |
| 2007/0232876 | A1 | 10/2007 | Otto et al. |
| 2007/0233395 | A1 | 10/2007 | Neel et al. |
| 2008/0114228 | A1 * | 5/2008 | McCluskey et al. .......... 600/365 |

FOREIGN PATENT DOCUMENTS

| | | |
|---|---|---|
| JP | 2001-052095 A | 2/2001 |
| JP | 2003-016182 A | 1/2003 |
| JP | 2003-108679 A | 4/2003 |
| JP | 2003-337863 A | 11/2003 |
| JP | 2004-220504 A | 8/2004 |
| JP | 2004-220504 A | 8/2004 |
| JP | 2004-252607 | 9/2004 |
| JP | 2006-217930 A | 8/2006 |
| JP | 2007-167648 A | 7/2007 |
| JP | 4023817 | 10/2007 |
| JP | 2007-304088 | 11/2007 |
| WO | 2006/122741 A2 | 11/2006 |

OTHER PUBLICATIONS

Office Action issued in corresponding Japanese Patent Application No. 2009-520331 dated Sep. 6, 2013.

Office Action issued in corresponding Japanese Patent Application No. 2009-520331 dated Jan. 20, 2015.

* cited by examiner

| Ward code | Measurement date | Measurement time | Blood glucose meter ID | Blood glucose level |
|---|---|---|---|---|
| xxxxx | 2008/1/12 | 9:05 | 112344 | 101 |
| xxxxx | 2008/1/12 | 11:55 | 112344 | 102 |
| xxxxx | 2008/1/12 | 9:01 | 113345 | 133 |
| xxxxx | 2008/1/12 | 12:03 | 113345 | 141 |
| xxxxx | 2008/1/12 | 20:10 | 113345 | 133 |
| xxxxx | 2008/1/12 | 8:50 | 123456 | 205 |
| xxxxx | 2008/1/12 | 11:51 | 123456 | 210 |
| xxxxx | 2008/1/12 | 8:45 | 145678 | 91 |
| xxxxx | 2008/1/12 | 11:48 | 145678 | 100 |
| yyyyy | 2008/1/12 | 9:04 | 234567 | 131 |
| yyyyy | 2008/1/12 | 11:55 | 234567 | 142 |
| yyyyy | 2008/1/12 | 20:50 | 234567 | 145 |
| yyyyy | 2008/1/12 | 8:03 | 251678 | 116 |
| yyyyy | 2008/1/12 | 11:45 | 251678 | 121 |
| yyyyy | 2008/1/12 | 20:42 | 251678 | 143 |
| yyyyy | 2008/1/12 | 8:12 | 325684 | 113 |
| yyyyy | 2008/1/12 | 12:08 | 325684 | 125 |
| yyyyy | 2008/1/12 | 20:48 | 325684 | 130 |
| yyyyy | 2008/1/12 | 7:58 | 102598 | 107 |
| yyyyy | 2008/1/12 | 12:02 | 102598 | 113 |

CODE READING DEVICE AND DATA COLLECTION SYSTEM USING THE SAME

The present application is a national stage of PCT International Application No. PCT/JP2009/051979, filed Feb. 5, 2009, and claims the benefit of Japanese Patent Application No. 2008-027358, filed Feb. 7, 2008.

TECHNICAL FIELD

The present invention relates to code information reading devices used for reading code information such as bar codes, and in particular to a code reading device capable of collecting data from a data holding device such as a measuring device and sending the collected data to a data processing device, and a measured data collection system using the code reading device.

BACKGROUND ART

Conventionally, in order to manage or compile data measured by measuring devices such as a blood glucose meter, there have been proposed mechanisms in which those measuring devices are connected to a data management system, and the data management system obtains the measured data from the measuring devices (see Japanese Patent No. 4,023,817 B, for example).

DISCLOSURE OF INVENTION

Problem to be Solved by the Invention

In such a system, the addition of various kinds of information, such as the date and time of the measurement and a patient identification, to the obtained data may be desired in order to manage the data accurately and effectively.

With the foregoing in mind, it is an object of the present invention to provide a code reading device capable of obtaining data from a data holding device, such as a measuring device, simply by connecting the code reading device to the data holding device and easily associating various kinds of information with the obtained data, and a data collection system using the code reading device.

Means for Solving Problem

In order to achieve the above object, a first code reading device according to the present invention is a code reading device that includes: a code reader for reading code information; a first connection portion for establishing connection with a data holding device; a second connection portion for establishing connection with a data processing device; a memory including a code information storage area for storing code information and a data storage area for storing obtained data; and a data processing control portion. When the code reader reads code information, the data processing control portion stores the read code information in the code information storage area of the memory. When a data holding device is connected to the first connection portion, the data processing control portion reads data from the connected data holding device and stores the data in the data storage area of the memory. When a data processing device is connected to the second connection portion, the data processing control portion sends to the data processing device the data in the data storage area in a state of being associated with the code information in the code information storage area.

In addition to measuring devices that generate measured data from external events and hold that the data, devices that hold internal data such as their operation statuses also are included in the scope of the data holding device. The internal data includes data indicating operation history at a normal state, failure information, error information or the like. According to the above configuration, code information read by the code reader is stored in the code information storage area of the memory of the code reading device, and data read from the data holding device is stored in the data storage area of the memory. And when the data processing device is connected to the code reading device, the code information and the data are sent to the data processing device in a state of being associated with each other. The code information and the data may be associated with each other when the data is stored in the memory of the code reading device or when the data is sent to the data processing device. Thus, by simply reading some kind of code information with the code reader, the code information can be collected by the data processing device in a state of being associated with data. The formats or contents of code information are not limited as long as the information can be read by the code reader. In addition to code readers using an optical reading format such as barcode readers that read two-dimensional or three-dimensional barcodes and Optical Character Recognition (OCR) readers, code readers with a variety of reading formats such as those that read codes magnetically and those that read codes electromagnetically like Radio Frequency Identification (RFID) can be adopted.

In order to achieve the above object, a second code reading device according to the present invention is a code reading device that includes: a code reader for reading code information; a first connection portion for establishing connection with a data holding device; a memory including a code information storage area for storing code information and a data storage area for storing obtained data; and a data processing control portion. When the code reader reads code information, the data processing control portion stores the read code information in the code information storage area of the memory. When a data holding device is connected to the first connection portion, the data processing control portion reads data from the connected data holding device and stores the data in the data storage area of the memory. The memory is a transportable memory that is readable by a data processing device, and when the memory is connected to the data processing device, the data in the data storage area is read by the data processing device in a state of being associated with the code information in the code information storage area.

Also in this configuration, code information read by the code reader is stored in the code information storage area of the memory of the code reading device, and the data read from the data holding device is stored in the data storage area in the transportable memory. And when the transportable memory is connected to the data processing device, the data processing device reads the code information and the data in a state of being associated with each other. The code information and the data may be associated with each other when the data is stored in the memory or when the data is read by the data processing device. Thus, by simply reading some kind of code information with the code reader, the code information can be collected by the data processing device in a state of being associated with data.

In the first and the second code reading devices according to the present invention, it is preferable that the code information storage area of the memory is formed to allow a plurality of pieces of code information to be stored therein, and when the data holding device is connected to the first connection portion, the data processing control portion stores data read from the data holding device in the data storage area by associating the data with any of the pieces of code information stored in the code information storage area.

For example, a measuring device, such as a blood glucose meter, can be used as the data holding device that is connected to the first and the second code reading devices according to the present invention. In this case, data measured by a measuring device such as a blood glucose meter is collected by the code reading device from the data holding device. Further, in this case, it is preferable that the code information is specification data of a control solution used in calibrating the blood glucose meter. This is because by associating the specification data of the control solution used in calibration with the measured data as code information, the traceability of the blood glucose meter can be easily managed.

For example, a device, such as an insulin pump, also can be used as the data holding device that is connected to the first and the second code reading devices according to the present invention. In this case, data that indicates operation statuses of the device such as an insulin supply status is collected by the code reading device from the data holding device.

Further, in the first and the second code reading devices according to the present invention, it is preferable that the data read by the data processing control portion from the data holding device includes an identifier for identifying the data holding device, when code information corresponding to new data is not read by the code reader, the data processing control portion makes reference to the memory and in the case that there is past data having the same identifier as that included in the data read from the data holding device, associates the code information associated with the past data with the new data as code information. According to this preferred configuration, once code information is read and stored in the code information storage area, upon collecting data from a data holding device having the same identifier, rereading of the code information can be omitted by using the code information associated with past data having an identifier as same as that of the data holding device.

The first and the second code reading devices according to the present invention further may include a display capable of displaying at least one of the code information and the data stored in the memory. According to this configuration, the code information and the data stored in the memory can be confirmed by using the display of the code reading device.

Further, in order to achieve the above object, a first data collection system according to the present invention is a data collection system that includes a code reading device, a data holding device, and a data processing device. The code reading device includes: a code reader for reading code information; a first connection portion for establishing connection with a data holding device; a second connection portion for establishing connection with a data processing device; a memory including a code information storage area for storing code information and a data storage area for storing obtained data; and a data processing control portion. When the code reader reads code information, the data processing control portion of the code reading device stores the read code information in the code information storage area of the memory. When a data holding device is connected to the first connection portion, the data processing control portion of the code reading device reads data from the connected data holding device and stores the data in the data storage area of the memory When a data processing device is connected to the second connection portion, the data processing control portion of the code reading device sends to the data processing device the data in the data storage area in a state of being associated with the code information in the code information storage area.

According to this system, when some kind of code information is read by the code reading device, the code information can be collected by the data processing device in a state of being associated with data.

Further, in order to achieve the above object, a second data collection system according to the present invention is a data collection system that includes a code reading device, a data holding device, and a data processing device. The code reading device includes: a code reader for reading code information; a first connection portion for establishing connection with a data holding device; a memory including a code information storage area for storing code information and a data storage area for storing obtained data; and a data processing control portion. When the code reader reads code information, the data processing control portion stores the read code information in the code information storage area of the memory. When a data holding device is connected to the first connection portion, the data processing control portion reads data from the connected data holding device and stores the data in the data storage area of the memory. The memory is a transportable memory that is readable by a data processing device, and when the memory is connected to the data processing device, the data in the data storage area is read by the data processing device in a state of being associated with the code information in the code information storage area.

According also to this system, when some kind of code information is read by the code reading device, the code information can be collected by the data processing device in a state of being associated with data.

Effects of the Invention

According to the present invention, it is possible to provide a code reading device that makes data management easy by collecting data from a data holding device through an easy operation of simply connecting the code reading device to the data holding device after finish reading code information and sending the collected data to a data processing device in a state of being associated with the read code information, and the data collection system using the code reading device.

DESCRIPTION OF THE INVENTION

Hereinafter, embodiments of the present invention will be described with reference to the drawings.

Embodiment 1

Figure 1A:
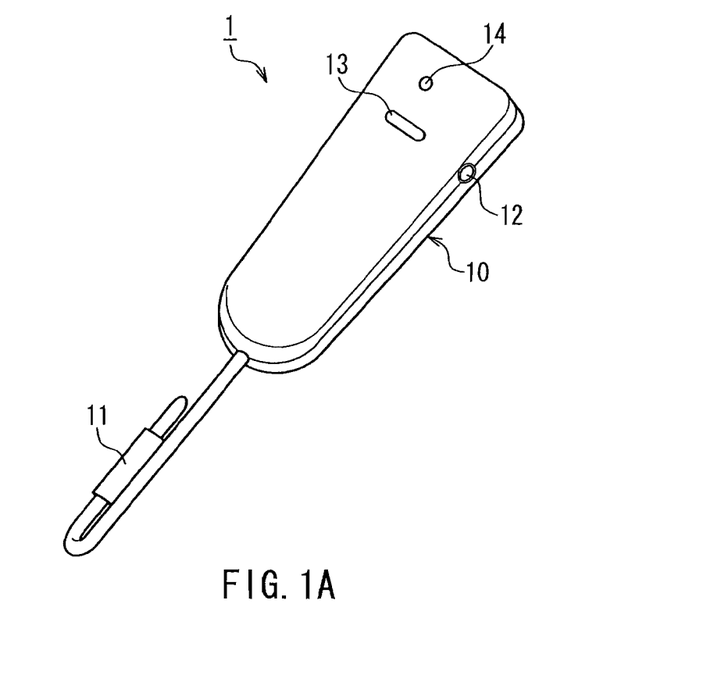
FIG. 1A is a perspective view showing the outer appearance of a code reading device according to Embodiment 1 of the present invention.
Figure 1B:
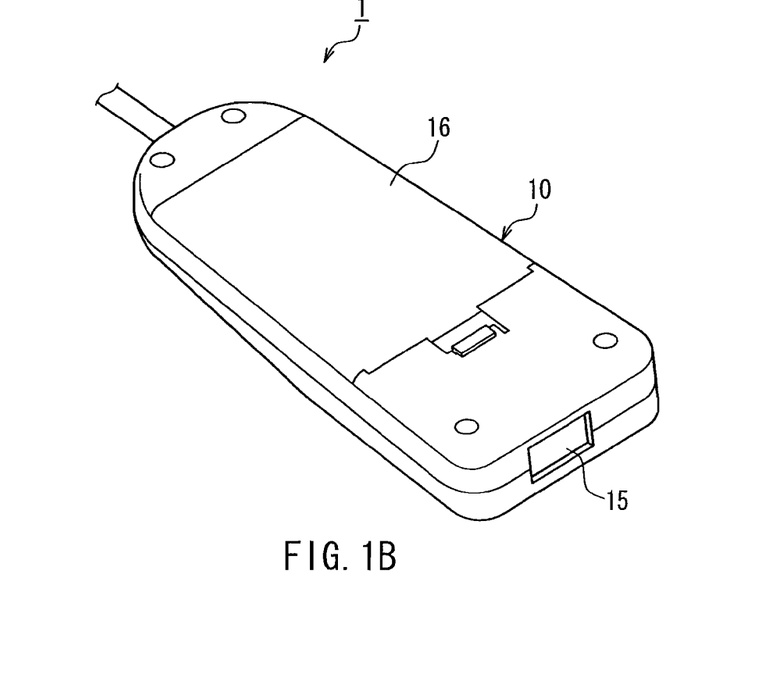
FIG. 1B is a perspective view showing the outer appearance of the code reading device according to Embodiment 1 of the present invention.

FIGS. 1A and 1B are perspective views showing the outer appearance of a code reading device 1 according to one embodiment of the present invention. As shown in FIG. 1A, the code reading device 1 includes, on a main body 10, a connection cable 11 (a first connection portion) for establishing connection with a blood glucose meter and a connection terminal 12 (a second connection portion) for establishing connection with a personal computer as a data processing device. An operation button 13 and a status indication LED 14 are provided on one surface of the main body 10.

It should be noted that, in the present embodiment, the blood glucose meter and the personal computer are used as a data holding device and the data processing device, respectively. However, the data holding device is not limited to the blood glucose meter, and also the data processing device is not limited to the personal computer. The data holding device is not limited to a measuring device such as the blood glucose meter, and an arbitrary device like an insulin pump that holds data such as its own operation status also is included in the scope of the data holding device, for example.

Further, as shown in FIG. 1B, a barcode reading portion (code reader) 15 is provided on a front-end portion of the main body 10. The barcode reading portion 15 includes a red LED and a C-MOS camera (both of them are not shown). When a user presses the operation button 13, the red LED irradiates a barcode with red light and the C-MOS camera reads the reflected light from the barcode, and thus the barcode is read. Although the status indication LED 14 indicates a reading status of a barcode or the like in the present embodiment, it is not an essential component. A lid 16, which is opened when replacing a battery, is provided on the back surface (the surface opposite to that provided with the operation button 13 and the status indication LED 14) of the main body 10.

Figure 2A:
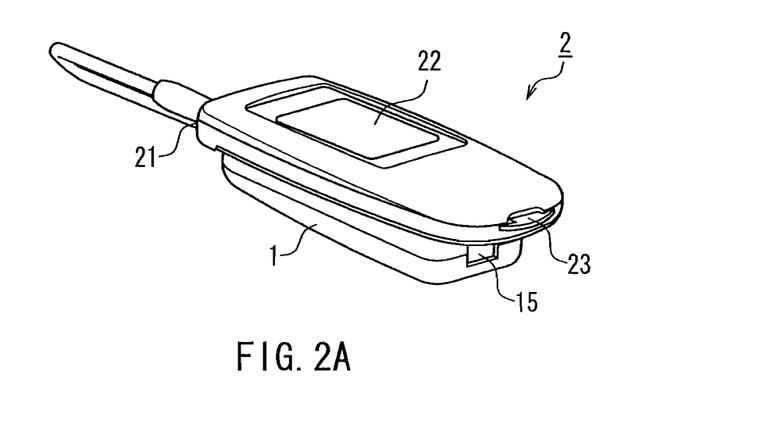
FIG. 2A is a perspective view showing a state in which the code reading device is connected to a blood glucose meter.
Figure 2B:
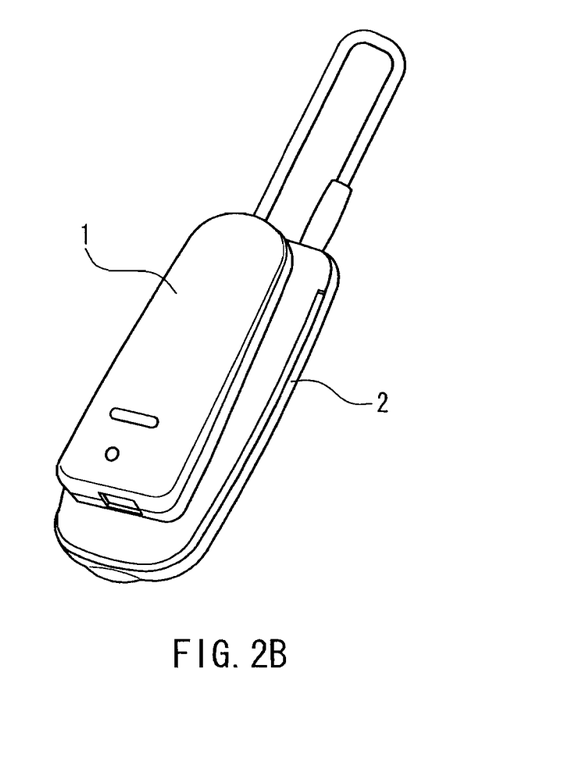
FIG. 2B is a perspective view showing a state in which the code reading device is connected to a blood glucose meter.

FIGS. 2A and 2B are perspective views showing a state in which the code reading device 1 is connected to a blood glucose meter 2. As shown in FIGS. 2A and 2B, the code reading device 1 is connected to the blood glucose meter 2 by inserting the connection cable 11 into a jack 21 of the blood glucose meter 2.

The blood glucose meter 2 includes a display 22 for displaying an operation menu, measurement results, and the like and a plug 23 into which a blood glucose level sensor is inserted. A user of the blood glucose meter 2 measures a blood glucose level by plugging a disposable blood glucose level sensor (not shown) into the plug 23, inserting a needle into a finger tip or the like to draw a trace amount of blood, and drawing the blood with the sensor.

The code reading device 1 can read barcodes even when it is not connected to the blood glucose meter 2 or it is connected to the blood glucose meter 2 as described above. Further, the blood glucose meter 2 can measure a blood glucose level even when the code reading device 1 is not connected thereto or the code reading device 1 is connected thereto. The blood glucose meter 2 includes a memory for storing blood glucose levels measured plural times along with the date and time information of the measurements. Further, a unique blood glucose meter ID is assigned to the blood glucose meter 2, and the ID is stored in its internal memory.

Figure 3:
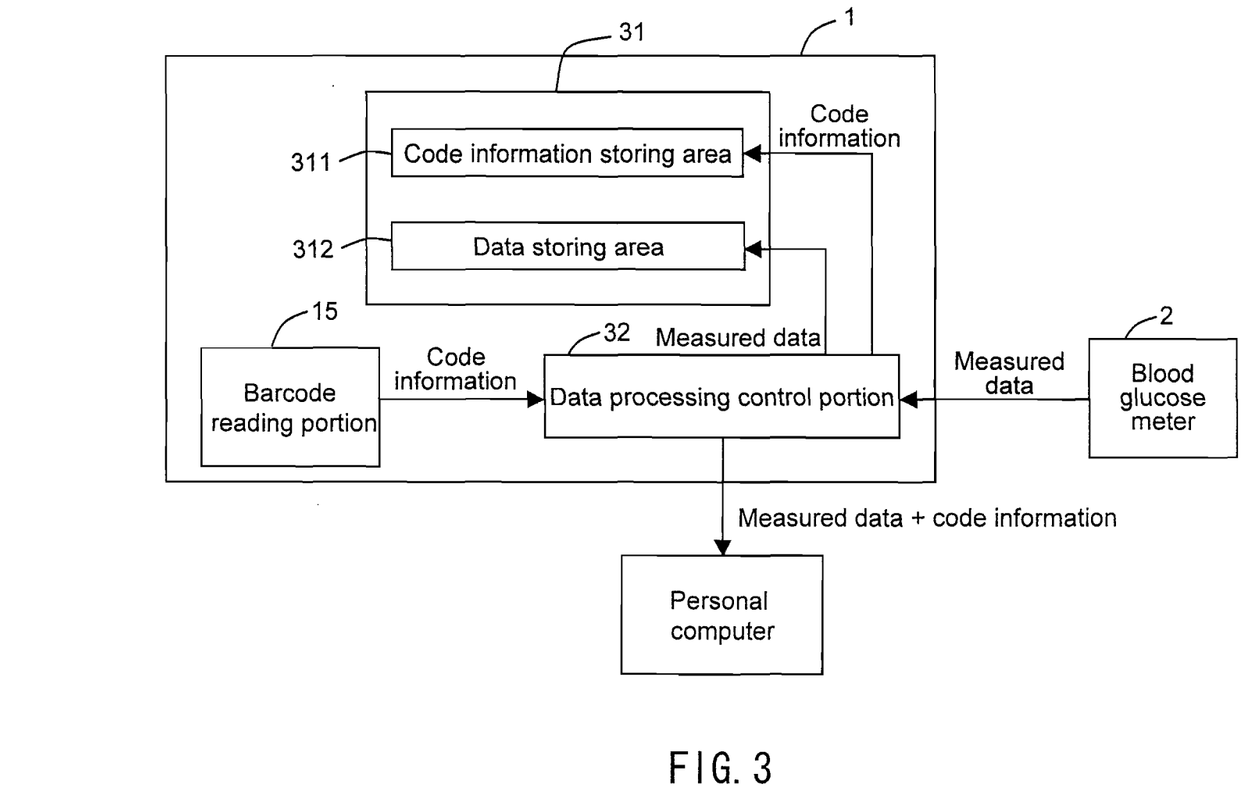
FIG. 3 is a block diagram schematically showing a functional configuration of the code reading device.

FIG. 3 is a block diagram schematically showing a functional configuration of the code reading device 1. As shown in FIG. 3, the code reading device 1 includes a memory 31 and a data processing control portion 32. The memory 31 includes an area 311 for storing code information indicated by a barcode read by the barcode reading portion 15, and an area 312 for storing measured data collected from the blood glucose meter 2. It should be noted that these areas 311 and 312 do not have to be physically separated areas. That is, the area 311 for storing code information and the area 312 for storing measured data may coexist in the memory 31 in a dispersed manner.

When the barcode reading portion 15 reads a barcode, the data processing control portion 32 stores in the area 311 of the memory 31 code information indicated by the read barcode. Further, when the blood glucose meter 2 is connected to the connection cable 11, the data processing control portion 32 reads measured data from the blood glucose meter 2 and stores the data in the area 312 of the memory 31. Furthermore, when the personal computer is connected to the connection terminal 12, the data processing control portion 32 associates the measured data in the area 312 with the code information stored in the area 311 and sends them to the personal computer.

It should be noted that the memory 31 is configured to allow the code information and the measured data to be stored therein in a state of being associated with each other. The data structure at this point can be determined arbitrarily. Thus, it may be a data structure in which code information to be associated with the measured data is stored as a whole as an item of each record of the measured data or it may be a data structure in which a stored location (address etc.) of code information to be associated with the measured data is stored as an item of each record of the measured data.

Figure 6:
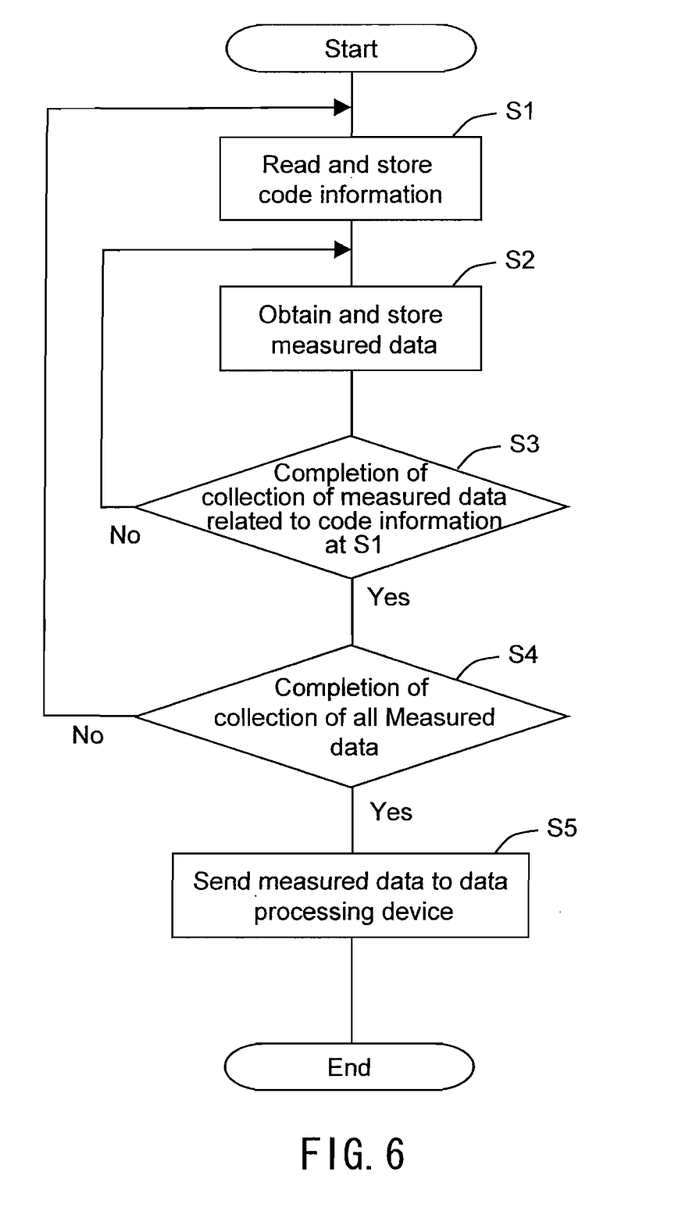
FIG. 6 is a flowchart showing a procedure of collection of measured data using the code reading device according to Embodiment 1.

Here, an example of use of the code reading device 1 will be described with reference to FIG. 6. The code reading device 1 according to the present embodiment can be used, for example, when collecting measured data from the blood glucose meters 2 individually owned by inpatients at a hospital or the like. For example, it is assumed that n-patients A1 to An in a ward A and m-patients B1 to Bm in a ward B measure their blood glucose level several times a day using the individually-owned blood glucose meters 2, and a nurse collects the measured data of these patients once a day.

In this case, a card or the like on which barcodes indicating the ward codes are printed is prepared in advance. First, the nurse reads the barcode indicating the ward code of the ward A from the card using the code reading device 1. The read ward code of the ward A is stored in the area 311 of the memory 31 (step S1). Next, the nurse makes rounds in the ward A carrying the code reading device 1 with the nurse.

Initially, the nurse connects the code reading device 1 to the blood glucose meter 2 of the patient A1, and thereby the measured data is sent from the blood glucose meter 2 of the patient A1 to the code reading device 1. The measured data is stored in the area 312 of the memory 31 along with the date and time of the measurements (step S2). At this time, the blood glucose meter ID of the blood glucose meter 2 also is collected along with the measured data and the like, and is stored in the area 312 of the memory 31. After completing the data collection from the blood glucose meter 2 of the patient A1, the nurse then connects the code reading device 1 to the blood glucose meter 2 of the patient A2 and performs data collection. Thereafter, by following a similar procedure, the nurse completes collection of the measured data of all of the patients A1 to An in the ward A (steps S2 to S3). Next, the nurse reads the barcode indicating the ward code of the ward B from the card. The read ward code of the ward B is stored in the area 311 of the memory 31. Then, the nurse makes rounds in the ward B carrying the code reading device 1 with the nurse, and collects the measured data of the patients B1 to Bm in the ward B by following a similar procedure as described above.

Figure 4:
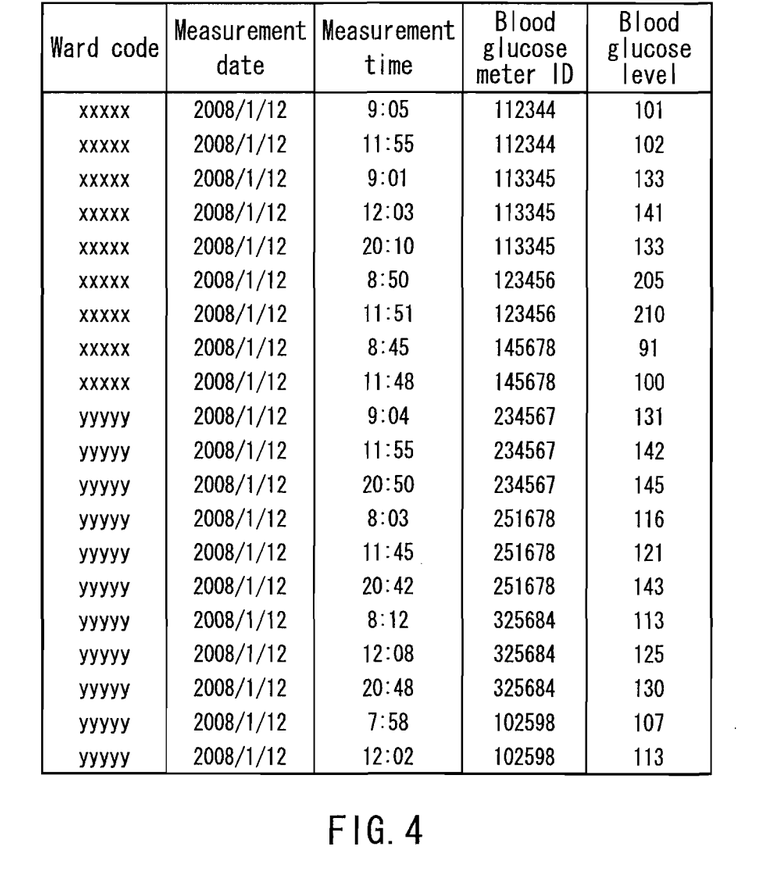
FIG. 4 is a schematic diagram showing an example of data stored in a memory of the code reading device.

Here, an example of the data stored in the memory 31 of the code reading device 1 is shown in FIG. 4. As shown in FIG. 4, the ward codes read from the barcodes and the data read from the blood glucose meters 2 owned by the patients in the respective wards are stored in the memory 31 in a state of being associated with each other. That is, each blood glucose level collected after reading the barcode indicating the ward code of the ward A is stored in the memory 31 in a state of being associated with the ward code xxxxx of the ward A. Further, each blood glucose level collected after reading the barcode indicating the ward code of the ward B is stored in the memory 31 in a state of being associated with the ward code yyyyy of the ward B. For example, "112344" is a blood glucose meter ID of the blood glucose meter 2 owned by the patient A1 and "113345" is a blood glucose meter ID of the blood glucose meter 2 owned by the patient A2.

After completing the data collection by following the above procedure (step S4), the nurse connects the code reading device 1 to a personal computer set in a nurse station or the like, and thereby the data stored in the memory 31 is sent from the code reading device 1 to the personal computer through the data processing control portion 32 (step S5). Thus, by simply establishing connection with the code reading device 1, the personal computer can collect the blood glucose level data of many patients with extreme ease. When the sending of the data from the memory 31 to the personal computer ends, the data processing control portion 32 may delete the data stored in the memory 31, so as to use the capacity of the memory 31 effectively.

As described above, according to the code reading device 1, code information read with the barcode reading portion 15 easily can be associated with measured data. In the above example, the ward code is used as code information. However, code information, which is read with the barcode reading portion 15 and associated with measured data, is not limited to this example. For example, various kinds of code information, such as code information for identifying an examination room, code information for identifying a hospital department, code information for identifying an attending doctor or nurse, and code information for identifying a patient may be read with the barcode reading portion 15 and associated with the measured data. Further, the number of code information to be associated with measured data is not limited to one, and more than one piece of code information may be read with the barcode reading portion 15 and associated with measured data. By associating various kinds of code information with measured data in this way, the traceability of the measured data can be improved. Further, since it requires only reading information in the form of a barcode, the operation is easy.

In the above example, it has been assumed that all of the patients own one blood glucose meter 2 each. However, instead of letting each of the patients own the blood glucose meter 2, the nurse may make rounds carrying the blood glucose meter 2 with the nurse and measure a plurality of the patients' blood glucose level. In this case, the nurse makes a visit to a patient carrying both the code reading device 1 and the blood glucose meter 2 with the nurse. Then, the nurse may read a patient ID from a card or a wrist band on which a barcode indicating the patient ID is printed using the code reading device 1, measure the blood glucose level of the patient on the spot using the blood glucose meter 2, and connect the code reading device 1 to the blood glucose meter 2. Or, the blood glucose level of the patient may be measured using the blood glucose meter 2 in a state of being connected to the code reading device 1. Consequently, it is possible to store the measured blood glucose level and the patient ID in the reading device 1 in a state of being associated with each other, and send them to the personal computer later on.

Further, the code reading device 1 also can be used in calibrating the blood glucose meter 2. Normally, the blood glucose meter 2 is calibrated by adhering, instead of blood, a glucose aqueous solution having a predetermined concentration called a control solution to a blood glucose level sensor, and measuring the sugar content of the solution. The manufacturer of the control solution used in the calibration prints in advance the specification data (concentration, expiration date, etc.) of the control solution on the bottle or the like in the form of barcodes. When performing the calibration, first, the barcodes on the bottle of the control solution are read with the code reading device 1, then the control solution is measured with the blood glucose meter 2, and finally, the code reading device 1 is connected to the blood glucose meter 2. Or, the control solution may be measured with the blood glucose meter 2 in the state of being connected to the code reading device 1. Thus, it is possible to store the measurement result of the control solution, the measured controlled glucose level, and the patient ID in the measuring device 1 in a state of being associated with each other, and send them to the personal computer later on.

Figure 5:
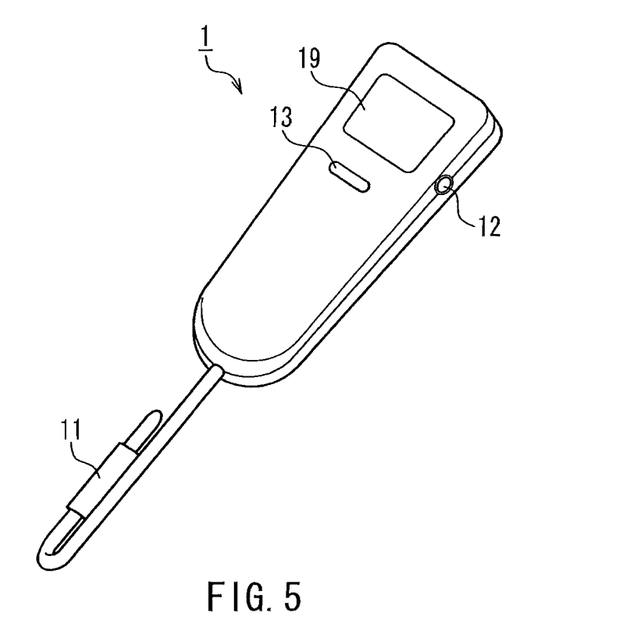
FIG. 5 is a perspective view showing the outer appearance of a modified example of the code reading device according to Embodiment 1.

It is also preferable to provide the code reading device 1 with a liquid crystal display 19 as shown in FIG. 5 to allow the code information and the measured data stored in the memory 31 to be displayed on the liquid crystal display 19. According to this configuration, it is possible to confirm code information at the time of reading a barcode, measured data itself at the time of reading the measured data from the blood glucose meter 2, or the association between the code information and the measured data. Although the liquid crystal display has been illustrated herein, the type of the display can be determined arbitrarily.

Further, although the memory 31 may be implemented by an internal memory of the code reading device 1, it also may be formed by a transportable memory having compatibility with both the code reading device 1 and the data processing device. For example, a variety of memory cards such as an USB memory and a SD card, a memory stick, and the like can be used as the transportable memory, although not limited only to these examples. In this case, instead of connecting the code reading device 1 to the data processing device, the transportable memory is removed from the code reading device 1, and then is connected to the personal computer so as to read the code information and the measured data in the transportable memory through the personal computer. However, in this case, since the data processing control portion 32 of the code reading device 1 does not involve in reading of the data from the memory 31 implemented by the transportable memory, it is necessary for the code information and the measured data to be associated with each other at the stage of storing the measured data in the memory 31 implemented by the transportable memory.

Embodiment 2

Hereinafter, Embodiment 2 of the present invention will be described. It should be noted that components having the same function as those described in Embodiment 1 will be denoted with the same reference numerals used in Embodiment 1, and the detailed description thereof will not be repeated.

The code reading device 1 according to the present embodiment is configured such that code information and measured data are stored in the memory 31 for a predetermined period or until an operator enters an instruction to delete them, so that the time and effort required in reading code information can be saved. For example, when the nurse makes rounds in a plurality of wards to collect measured data as in the specific example given in Embodiment 1, it is not necessary to read the ward codes every time if the wards in which the nurse makes rounds are always the same.

Figure 7:
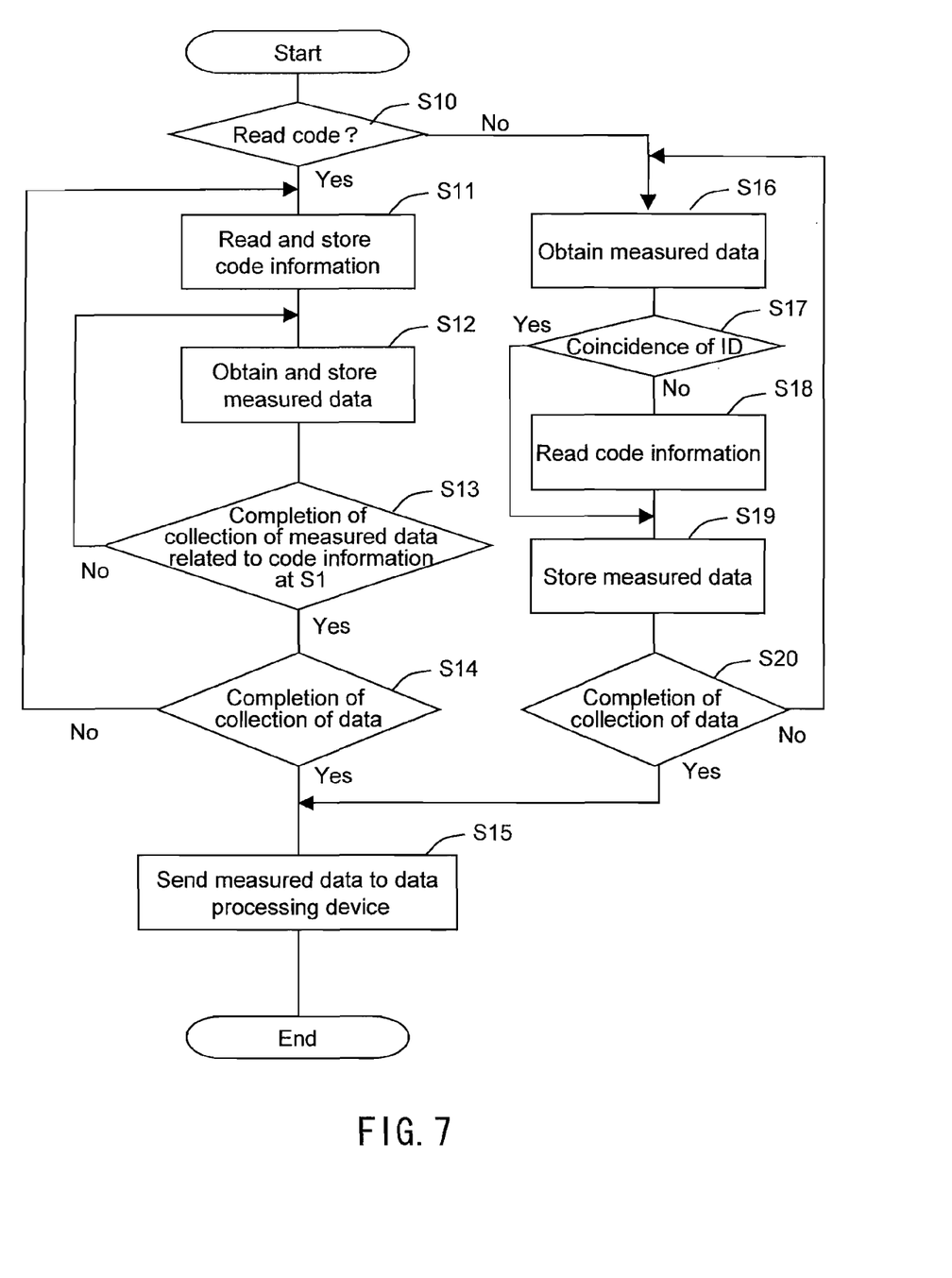
FIG. 7 is a flowchart showing a procedure of collection of measured data using a code reading device according to Embodiment 2 of the present invention.

Therefore, the data processing control portion 32 of the code reading device 1 according to the present embodiment operates as follows. FIG. 7 is a flow chart showing the operation of the code reading device 1 according to the present embodiment.

In the present embodiment, first, an operator selects whether to read code information or not (step S10). For example, when the code reading device 1 is provided with the liquid crystal display 19 as shown in FIG. 5, a message or the like that asks the operator whether to read the code information or not may be displayed on the liquid crystal display 19 and lets the operator make the selection. Or, the code reading device 1 may be provided with a special mechanical switch that is pressed when the code information needs to be read, and the operator can press the switch when the code information needs to be read.

For example, when using the code reading device 1 for the first time, the operator needs to select reading the code information at step 10. In this case, similarly to Embodiment 1, the nurse reads, for example, a barcode indicating the ward code of the ward A using a card or the like on which the barcode indicating the ward code is printed. The read ward code of the ward A is stored in the area 311 of the memory 31 (step S11). Next, the nurse makes rounds in the ward A carrying the code reading device 1 with the nurse, and collects measured data from the blood glucose meters 2 of the patients in the ward A by following a similar procedure to that described in Embodiment 1 (steps S12 to S13). After completing the collection of the measured data in the ward A, the nurse reads a barcode indicating the ward code of the ward B, and collects measured data from the blood glucose meters 2 of the patients in the ward B by following a similar procedure to that described in Embodiment 1. Then, after completing the data collection from the blood glucose meters 2 of all of the patients in the wards A and B (Yes at step S14), by connecting the code reading device 1 to a personal computer, the data stored in the memory 31 of the code reading device 1 is sent to the personal computer, similarly to Embodiment 1 (step S15).

In the present embodiment, even after the data stored in the memory 31 is sent to the personal computer at step S15, the data in the memory 31 remains undeleted. Although a period for saving the data in the memory 31 depends on the capacity of the memory, it may be configured to allow the period for holding the data in the memory 31 to be set or to save the data until the operator enters a clear instruction to delete the data in the memory 31.

As described above, once the code information is read, the nurse does not have to read the code information in the next data collection. That is, for example, when measured data is collected again on the next day after measured data was collected by following steps S11 to S15 described above, the nurse selects not to read the barcodes at step S10. Consequently, the process goes to step S16. At step 16, measured data is collected from the blood glucose meter 2 of a patient (step S16). As described in Embodiment 1, the measured data in the blood glucose meter 2 is read by the code reading device 1 along with the blood glucose meter ID. The data processing control portion 32 of the code reading device 1 searches the data storage area 312 of the memory 31 using the read blood glucose meter ID as a search key to determine whether measured data having the same blood glucose meter ID has been registered or not (step S17).

When the result at step S17 is No, in other words, when measured data having the same blood glucose meter ID as the newly collected measured data has not been registered in the data storage area 312 of the memory 31, the code reading device 1 sends an instruction to the operator to read code information (ward code) (step S18). It should be noted that the instruction to the operator may be implemented by using an arbitrary means such as displaying an instruction message on the liquid crystal display 19 of the code reading device 1 or instructing the operator by voice. The read code information is associated with the newly collected measured data at step S19 which will be described later, and recored in the memory 31.

In contrast, when the result at step S17 is Yes, code information (ward code) associated with the measured data in the data storage area 312 is obtained, and the obtained ward code is associated with the measured data collected this time at step S16 as its ward code, and recorded in the memory 31 (step S19).

Then, after completing the data collection from the blood glucose meters 2 (step S20), the process goes to step S15, and the data in the memory 31 is sent to the personal computer.

It should be noted that, in the present embodiment, when the data is read from the memory 31 and sent to the personal computer at step S15, the past data is also remaining in the memory 31. Thus, it is preferable to read only the new measured data by extracting the new measured data and excluding the data that already has been sent in the past. Thus, a flag that indicates whether a record already has been sent to the personal computer or not may be set to each measured data record in the data storage area 312 of the memory 31.

As described above, according to the code reading device 1 according to Embodiment 2, when past measured data having the same blood glucose meter ID as newly collected measured data has been stored in the memory 31, the code information associated with the past measured data can be used as the code information of the newly collected measured data. Thus, since the code information does not need to be read every time, an operator's time and effort can be saved.

In the example shown in FIG. 7, in order to enable determination of whether the code information corresponding to the new data has been read or not, whether to read code information or not is selected by the operator at step S10. However, instead of letting the operator make such a selection explicitly, by clearing the contents in the code information storage area 311 of the memory 31 when sending of the measured data is completed at step S15, at the next time whether the code information corresponding to the new data has been read or not may be determined on the basis of whether significant code information has been stored in the code information storage area 311 or not.

Embodiment 3

Hereinafter, yet another embodiment of the present invention will be described.

The code reading device 1 according to the present embodiment not only can collect data from a data holding device directly mounted thereon but also can collect data indirectly from other devices connected to the data holding device or other devices capable of communicating with the data holding device. Examples of such "other devices" include, for example, an insulin pump used in relation to the blood glucose meter 2. An insulin pump is a device that is connected to a tube introduced into the abdomen or the like of a diabetic to keep supplying insulin in a trace amount (an amount corresponding to basal secretion) at all times.

Figure 8:
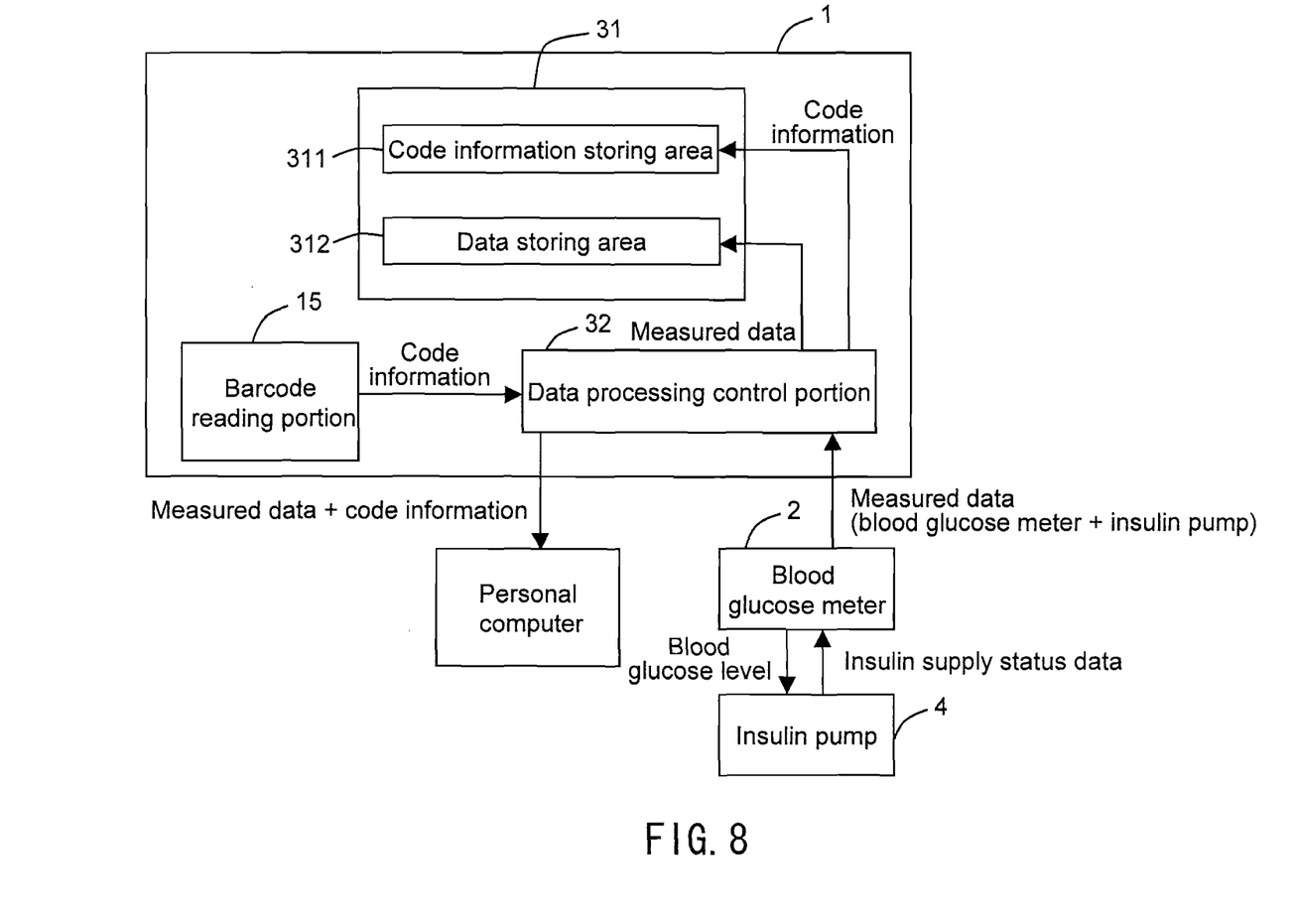
FIG. 8 is a block diagram schematically showing a functional configuration of a data collection system according to Embodiment 3 of the present invention.

In the present embodiment, an insulin pump 4 is connectable to the blood glucose meter 2 as shown in FIG. 8. Further, the blood glucose meter 2 in the present embodiment is a blood glucose meter having a subcutaneous sensor. Thus, patients' blood glucose level can be measured at all times. In a case of such the blood glucose meter having the subcutaneous sensor, the main body of the blood glucose meter 2 is capable of communicating with the sensor implanted in a patient through a cable or radio. In the latter case, i.e., in the case of radio communication, the main body of the blood glucose meter 2 also can be configured as a device such as a wrist watch or a portable information terminal device that has other function in addition to measuring a blood glucose level. Further, both the blood glucose meter 2 and the insulin pump 4 may be configured to exchange data and instructions through radio communication.

In the present embodiment, the blood glucose meter 2 monitors variations in a blood glucose level of a patient and the insulin pump 4 controls a supply of insulin so that the blood glucose level of the patient can be controlled properly on the basis of the blood glucose level measured by the blood glucose meter 2. Insulin supply status data is sent to the blood glucose meter 2 from the insulin pump 4 at all times. The insulin supply status data may include, for example, a device ID for identifying the insulin pump 4, in addition to data such as the supply time and the supply of insulin. The blood glucose meter 2 stores the insulin supply status data received from the insulin pump 4 in its internal memory And when the code reading device 1 is connected to the blood glucose meter 2, the insulin supply status data stored in the internal memory is sent to the code reading device 1 along with the measured data of the blood glucose level described in Embodiment 1.

According to the configuration of the present embodiment, the insulin supply status data of the insulin pump 4 also can be collected through the blood glucose meter 2 by connecting the code reading device 1 to the blood glucose meter 2.

In the present embodiment, the insulin pump 4 has been used as an example of a device whose data is collected and held by the blood glucose meter 2. However, in addition to an insulin pump, a device such as a pulse meter, a pedometer, a manometer, or an electrocardiograph can be used as the device whose data is collected and held by the blood glucose meter 2, although not limited only to these examples.

Each of the embodiments is merely an example of the present invention and does not limit the technical scope of the present invention. For example, in the above description, a barcode has been used as an example of the code information. However, the code information is not limited to this example and an arbitrary code reader may be used in accordance with the type of code information to be used. For example, when a two dimensional barcode is used as the code information, a reader that reads two-dimensional barcodes may be provided. It is also possible to use a three dimensional barcode such as a QR code. Further, the code information is not limited to optically readable code information such as the barcodes and OCR, and codes that are read electromagnetically or magnetically such as RFID and a magnetic code can also be used.

In each of the above embodiments, the case in which the nurse collects measured data from patients' blood glucose meters at the hospital has been described as an example. However, the code reading device of the present invention is not limited to this application and can be used to collect arbitrary data at an arbitrary place.

The invention claimed is:

1. A code reading device comprising:
   a code reader for reading code information;
   a first connection portion for establishing connection with a blood glucose meter, the first connection portion being configured so as to input data from the blood glucose meter, and wherein the blood glucose meter generates a blood glucose level as the data and holds the data, the blood glucose meter compromises a plug, and blood drawn with a blood glucose level sensor into the plug is used to measure a blood glucose level, thereby the code reading device goes not generate a blood glucose level;
   a second connection portion for establishing connection with a data processing device;
   a memory including a code information storage area for storing code information and a data storage area for storing obtained data; and
   a data processing control portion,
   wherein when the code reader reads code information, the data processing control portion stores the read code information in the code information storage area of the memory,
   when the blood glucose meter is connected to the first connection portion, the data processing control portion reads data from the connected blood glucose meter and stores the data in the data storage area of the memory, and
   when a data processing device is connected to the second connection portion, the data processing control portion sends to the data processing device the data in the data storage area in a state of being associated with the code information in the code information storage area.

2. The code reading device according to claim 1,
   wherein the code information storage area of the memory is formed to allow a plurality of pieces of code information to be stored therein, and
   when the blood meter is connected to the first connection portion, the data processing control portion stores data read out from the blood glucose meter in the data storage area by associating the data with any of the pieces of code information stored in the code information storage area.

3. The code reading device according to claim 1, wherein the code information is specification data of a control solution used in calibrating the blood glucose monitor.

4. The code reading device according to claim 1,
   wherein the data read by the data processing control portion from the blood glucose meter includes an identifier for identifying the blood glucose meter,
   when code information corresponding to new data is not read by the code reader, the data processing control portion makes reference to the memory and, in the case that there is past data having an identifier as same as that included in the data read from the blood glucose meter, associates the code information associated with the past data with the new data as code information.

5. The code reading device according claim 1 further comprising a display capable of displaying at least one of the code information and the data stored in the memory.

6. The code reading device according to claim 1, wherein the first connection portion is constituted with a connection cable.

7. A code reading device comprising:
a code reader for reading code information;
a first connection portion for establishing connection with blood glucose meter, the first connection portion being configured so as to input data from the blood glucose meter, and wherein the blood glucose meter generates blood glucose level as the data and holds the data the blood glucose meter compromises a plug, and blood drawn with a blood glucose level sensor plugged into the plug is used to measure a blood glucose level, thereby code reading device does not generate a blood glucose level;
a memory including a code information storage area for storing code information and a data storage area for storing obtained data; and
a data processing control portion,
wherein when the code reader reads code information, the data processing control portion stores the read code information in the code information storage area of the memory,
when the blood glucose meter is connected to the first connection portion, the data processing control portion reads data from the connected blood glucose meter and stores the data in the data storage area of the memory, and
the memory is a transportable memory that is readable by a data processing device, and when the memory is connected to the data processing device, the data in the data storage area is read by the data processing device in a state of being associated with the code information in the code information storage area.

8. The code reading device according to claim 7, wherein the code information storage area of the memory is formed to allow a plurality of pieces of code information to be stored therein, and
when the blood glucose meter is connected to the first connection portion, the data processing control portion stores data read out from the blood glucose meter in the data storage area by associating the data with any of the pieces of code information stored in the code information storage area.

9. The code reading device according to claim 7, wherein the data read by the data processing control portion from the blood glucose meter includes an identifier for identifying the blood glucose meter,
when code information corresponding to new data is not read by the code reader, the data processing control portion makes reference to the memory and, in the case that there is past data having an identifier as same as that included in the data read from the blood glucose meter, associates the code information associated with the past data with the new data as code information.

10. The code reading device according to claim 7 further comprising a display capable of displaying at least one of the code information and the data stored in the memory.

11. The code reading device according to claim 7, wherein the first connection portion is constituted with a connection cable.

12. A data collection system comprising a code reading device, a blood glucose meter, and a data processing device, wherein the code reading device includes:
a code reader for reading code information;
a first connection portion for establishing connection with a blood glucose meter, the first connection portion being configured so as to input data from the blood glucose meter, and wherein the blood glucose meter generates a blood glucose level as the data and holds the data, the blood glucose meter comprises a plug, and blood drawn with a blood glucose level sensor plugged into the plug is used to measure a blood glucose level, thereby the code reading device does not generate a blood glucose level;
a second connection portion for establishing connection with a data processing device;
a memory including a code information storage area for storing code information and a data storage area for storing obtained data; and
a data processing control portion,
when the code reader reads code information, the data processing control portion of the code reading device stores the read code information in the code information storage area of the memory,
when the blood glucose meter is connected to the first connection portion, the data processing control portion of the code reading device reads data from the connected blood glucose meter and stores the data in the data storage area of the memory, and
when a data processing device is connected to the second connection portion, the data processing control portion of the code reading device sends to the data processing device the data in the data storage area in a state of being associated with the code information in the code information storage area.

13. The data collection system according to claim 12, wherein the first connection portion is constituted with a connection cable.

14. A data collection system comprising a code reading device, a blood glucose meter, and a data processing device,
wherein the code reading device includes:
a code reader for reading code information;
a first connection portion for establishing connection with a blood glucose meter, the first connection portion being configured so as to input data from the blood glucose meter, and wherein the blood glucose meter generates a blood glucose level as the data and holds the data, the blood glucose meter comprises a plug, and blood drawn with a blood glucose level sensor plugged into the plug is used to measure a blood glucose level, thereby code reading device does not generate a blood glucose level;
a memory including a code information storage area for storing code information and a data storage area for storing obtained data; and
a data processing control portion,
wherein when the code reader reads code information, the data processing control portion stores the read code information in the code information storage area of the memory,
when the blood glucose meter is connected to the first connection portion, the data processing control portion reads data from the connected blood glucose meter and stores the data in the data storage area of the memory, and
the memory is a transportable memory that is readable by a data processing device, and when the memory is connected to the data processing device, the data in the data storage area is read by the data processing device in a state of being associated with the code information in the code information storage area.

15. The data collection system according to claim 14, wherein the first connection portion is constituted with a connection cable.

16. A code reading device comprising:
a code reader for reading code information;
a first connection portion for establishing connection with a blood glucose meter, the first connection portion is constituted with a connection cable, the first connection portion being configured so as to input data from the blood glucose meter, and wherein the blood glucose meter generates a blood glucose level as the data and holds the data, the blood glucose meter comprises a plug, and blood drawn with a blood glucose level sensor plugged into the plug is used to measure a blood glucose level;
a second connection portion for establishing connection with a data processing device;
a memory including a code information storage area for storing code information and a data storage area for storing obtained data; and
a data processing control portion;
wherein when the code reader reads code information, the data processing control portion stores the read code information in the code information storage area of the memory,
when the blood glucose meter is connected to the first connection portion, the data processing control portion reads data from the connected blood glucose meter and stores the data in the data storage area of the memory, and
when a data processing device is connected to the second connection portion, the data processing control portion sends to the data processing device the data in the data storage area in a state of being associated with the code information in the code information storage area.

17. A code reading device comprising:
a code reader for reading code information;
a first connection portion for establishing connection with a blood glucose meter, the first connection portion is constituted with a connection cable, the first connection portion being configured so as to input data from the blood glucose meter, and wherein the blood glucose meter generates a blood glucose level as the data and holds the data, the blood glucose meter comprises a plug, and blood drawn with a blood glucose level sensor plugged into the plug is used to measure a blood glucose level;
a memory including a code information storage area for storing code information and a data storage area for storing obtained data; and
a data processing control portion;
wherein when the code reader reads code information, the data processing control portion stores the read code information in the code information storage area of the memory,
when the blood glucose meter is connected to the first connection portion, the data processing control portion reads data from the connected blood glucose meter and stores the data in the data storage area of the memory, and
the memory is a transportable memory that is readable by a data processing device, and when the memory is connected to the data processing device, the data in the data storage area is read by the data processing device in a state of being associated with the code information in the code information storage area.

18. A data collection system comprising a code reading device, a blood glucose meter, and a data processing device, wherein the code reading device includes:
a code reader for reading code information;
a first connection portion for establishing connection with a blood glucose meter, the first connection portion is constituted with a connection cable, the first connection portion being configured so as to input data from the blood glucose meter, and wherein the blood glucose meter generates a blood glucose level as the data and holds the data, the blood glucose meter comprises a plug, and blood drawn with a blood glucose level sensor plugged into the plug is used to measure a blood glucose level;
a second connection portion for establishing connection with a data processing device;
a memory including a code information storage area for storing code information and a data storage area for storing obtained data; and
a data processing control portion;
when the code reader reads code information, the data processing control portion of the code reading device stores the read code information in the code information storage area of the memory,
when the blood glucose meter is connected to the first connection portion, the data processing control portion of the code reading device reads data from the connected blood glucose meter and stores the data in the data storage area of the memory, and
when a data processing device is connected to the second connection portion, the data processing control portion of the code reading device sends to the data processing device the data in the data storage area in a state of being associated with the code information in the code information storage area.

19. A data collection system comprising a code reading device, a blood glucose meter, and a data processing device, wherein the code reading device includes:
a code reader for reading code information;
a first connection portion for establishing connection with a blood glucose meter, the first connection portion is constituted with a connection cable, the first connection portion being configured so as to input data from the blood glucose meter, and wherein the blood glucose meter generates a blood glucose level as the data and holds the data, the blood glucose meter comprises a plug, and blood drawn with a blood glucose level sensor plugged into the plug is used to measure a blood glucose level;
a memory including a code information storage area for storing code information and a data storage area for storing obtained data; and
a data processing control portion;
wherein when the code reader reads code information, the data processing control portion stores the read code information in the code information storage area of the memory,
when the blood glucose meter is connected to the first connection portion, the data processing control portion reads data from the connected blood glucose meter and stores the data in the data storage area of the memory, and
the memory is a transportable memory that is readable by a data processing device, and when the memory is connected to the data processing device, the data in the data storage area is read by the data processing device in a state of being associated with the code information in the code information storage area.

* * * * *